United States Patent [19]

Weisler

[11] Patent Number: 4,876,090

[45] Date of Patent: Oct. 24, 1989

[54] SYSTEMIC INSECT REPELLENT COMPOSITION AND METHOD

[76] Inventor: Richard Weisler, 8690 N.W. 56th St., Coral Springs, Fla. 33065

[21] Appl. No.: 98,686

[22] Filed: Sep. 21, 1987

[51] Int. Cl.$^4$ .................. A61K 35/78; A61K 31/51
[52] U.S. Cl. ...................... 424/195.1; 514/276; 514/875
[58] Field of Search ............ 574/276; 424/195.1, 424/DIG. 10; 514/255, 918, 875, 919

[56] References Cited

U.S. PATENT DOCUMENTS

4,455,304  6/1984  Yaralian ........................ 424/195.1
4,702,914  10/1987  Ryan ............................... 514/255

OTHER PUBLICATIONS

"Flea Control" by Moira Anderson, *Dog Fancy*, vol. 18, No. 6, (Jun. 1987), pp. 24 to 33.
Butler et al., *The Best Medicine*, pp. 431–432, 517–519, (1985).

The Merck Index., 10th Ed., p. 45, number 291 (1983).
The Merck Index., 10th Ed., p. 1451, number 9904 (1983).
The Merck Index., 10th Ed., p.624, number 4232 (1983).

*Primary Examiner*—Douglas W. Robinson
*Assistant Examiner*—R. Kearse
*Attorney, Agent, or Firm*—John H. Faro

[57] ABSTRACT

A systemic insect repellent composition is provided which affords essentially continuous protection of domesticated animals against fleas, ticks and other blood feeding pests. The systemic compositions of the invention comprise two essential ingredients: Vitamin $B_1$ and allyl sulfide (garlic oil) dissolved in a soybean oil base. The composition is preferably consumed by the animal during its normal feeding. The dosage consumed by the animal is adjusted to provide a prescribed minimal blood level which insures continuous insect repellency. Unlike the more popular preparations, this composition is not inherently toxic, is not offensive to the animal and does not give the animal bad breath.

11 Claims, No Drawings

SYSTEMIC INSECT REPELLENT COMPOSITION AND METHOD

BACKGROUND OF THE INVENTION

1. Field of the Invention

This invention relates to a composition and to a method. More specifically, this invention is directed to a natural, nutritional composition comprising a synergistic mixture of vitamin $B_1$ and allyl sulfide (garlic oil) dissolved in a natural vegetable oil vehicle (soybean oil). The synergistic mixture of this composition is ingested at meal time and rapidly absorbed into the blood. The appropriate dosage at meal time results in a discrete odor being continuously released through the surface of the skin, which is repellent of fleas and ticks. This odor is otherwise undetectable.

2. Description of the Prior Art

Flea infestation of household pets (cats & dogs) and other domesticated animals has been an apparently insoluble problem for both the pet owner and the veterinary professional. A variety of synthetic chemicals have been developed and prescribed for control of flea and tick infestation. Some of the agents are intended for topical applications while others are ingested. Most of the synthetic preparations are poisons and can thus evoke toxic (adverse) reactions in both the treated animal and in the pet owner. In addition, these chemicals carry environmental hazard warnings. Insects tend to build up mutagenic immunity to these chemicals rendering them useless after several weeks.

Because of increasing public awareness of the potential hazard of long term exposure to such toxic agents, natural products for control of flea infestations have received greater consumer acceptance. Natural flea control products include certain consumable preparations which range in composition from complex mixtures, such as Brewer's yeast to vitamin B complex. These preparations are generally combined with other dietary supplements and certain other ingredients to enhance their pet appeal.

Garlic in the form of tablets has also been suggested as a dietary supplement for the control of fleas. Because of the naturally offensive odor of this substance, it is often deodorized to render it less unpalatable and thereby enhance its pet appeal.

Other natural products which have been suggested for the control of fleas include herbal oils, which are used as a topical repellent. These oils can be applied to a cloth flea collar. One such preparation, available from ECOSAFE Laboratories under the brand name "Insect Shoo", reportedly contains citronella, cedarwood, orange eucalyptus and bay oils. The use of cedar chips in pet bedding is also reportedly effective in repelling fleas. Other natural flea repellent treatments include lemon dips; and, rubbing lemon juice into the pet's coat on a periodic basis (every 2-3 days).

The attach on this persistent pest has most recently been waged with ultrasonics. The miniaturization of ultrasonic sound transmitters and their incorporation into a flea collar has proven to be surprisingly effective in a number of instances.

While all the foregoing synthetic and naturally occurring topical and systemic treatments are effective to a degree, each suffers from one or more shortcomings and may in certain instances evoke an adverse reaction in the pet, the pet owner or both. The adaptations of ultrasonic sound to this problem is by no means a panacea. While the initial investment in this device is substantial, it is by no means effective in all environments and, of course, requires periodic replacement of the transmitter batteries. When the battery power begins to decay, the effectiveness of this device is also diminished, thus, resulting in reinfestation of the pet. Where the pet resides within the house, the household environment is once again exposed to these pests and must be fumigated. The collar contains a large bulky box which is worn around the neck which is particularly bothersome to smaller dogs and to cats.

As is thus evident, there is an unfilled need for a safe and effective flea repellent which operates continuously and with little if any pet or owner inconvenience. Such repellent should also preferably comprise a natural composition which is safe and effective, and yet does not perceptibly alter the animal's appearance, breath or otherwise detract from the pleasure of pet ownership.

OBJECTS OF THE INVENTION

It is the object of this invention to remedy the above as well as related deficiencies in the prior art.

More, specifically, it is the principle object of this invention to provide a natural flea repellent composition which can be ingested during routine feeding, and provides essentially continuous systemic control of fleas and ticks.

It is another of the objects of this invention to provide a natural flea repellent composition in which the individual functional components are rapidly and efficiently absorbed from the digestive track into the blood stream.

It is yet another object of this invention to provide a natural flea repellent composition, in a precise dosage form, which can be ingested during routine feeding.

It is still another object of this invention to provide a natural flea repellent composition which need not be pre-treated or altered from its natural state and thereby retains its inherent flea repellent properties.

Additional objects of this invention include the systemic treatment of flea infested mammals with the flea repellent composition of this invention.

SUMMARY OF THE INVENTION

The above and related objects of this invention are achieved by providing a dietary supplement consisting essentially of aneurine (Vitamin $B_1$) and allium sativum (oil of garlic). It is understood that the active ingredient which is contributed by the oil of garlic is allyl sulfide and that allyl sulfide from any source can be substituted for the oil of garlic in this dietary supplement. Of course where such substitution is made, a comparable amount of allyl sulfide will be required. The functional components of this composition are combined in the appropriate relative proportions in a vegetable oil base and the resultant solution thereafter placed in a water soluble capsule (gelatin). The relative quantities of each of the functional components in this composition is believed to be of critical significance as is the synergism between them. In order to maintain an effective and relatively constant systemic level of this composition, it is administered at periodic intervals (preferably every 12 hours) on a daily basis. In the preferred embodiments of this invention, an effective flea repellent, daily dose of this composition will contain at least about 1 mg of aneurine and at least about 21 mg of allium sativum per pound of animal body weight.

DESCRIPTION OF THE INVENTION INCLUDING PREFERRED EMBODIMENT

Preliminary to further discussion of this invention, it would be helpful to briefly discuss a number of terms and phrases which are used throughout the text of this disclosure.

The phrases "flea repellent" and "insect repellent" as used herein, are intended as descriptive of the action of the composition of this invention, when taken internally, to exude an odor through the skin of the animal which is offensive to fleas and ticks, thus, controlling and, in most instances, eliminating infestation of the animal by such pests.

The terms "sinergist" and "synergism" as used herein, are intended as descriptive of the enhanced insect repellent protection of the individual functional components when used in conjunction with one another in the composition this invention.

The phrase "allium sativum" as used herein, is intended as descriptive of oil of garlic and garlic-like plants which are readily absorbed from the digestive tract into the blood stream and release an imperceptible odor through the skin of an animal which is offensive to blood feeding insects such as fleas and ticks.

The term "aneurine" as used herein is intended as descriptive of Vitamin $B_1$, which is readily absorbed from the digestive tract into the blood stream and releases an imperceptible odor through the skin of the animal which is offensive to insects such as fleas and ticks.

The phrase "insect repellent effective amount" as used herein is intended as descriptive of the quantity of the composition of this invention which is administered to the animal to achieve a blood level of insect repellent ingredients which is effective to control/eliminate flea infestation.

The preferred composition of this invention consists essentially of aneurine and allium sativum, in predetermined relative proportions, dissolved in a vegetable oil carrier. The composition is unique in a number of respects which permit delivery of an efficacious amount of the composition, in a precise dosage form, thereby permitting predictable results in a field which has been largely the domain of the empiricist. Because the functional components of this composition are soluble in the vegetable oil carrier and also readily soluble in the environment of the small intestine, their rate and completeness of absorption into the blood stream is greatly facilitated. The functional ingredients of this composition and/or their respective metabolites release an odor through the skin which effectively repels fleas and ticks.

The administration of periodic dosages of this composition with meals/snacks insures the maintenance of an efficacious level of flea repellent within the systemic system of the affected animal.

The compositions of this invention offer unique and improved treatment of mammals for blood feeding pests such as ticks, fleas and the like. One of the unique and advantageous features of the compositions is the method of administration of the composition in a precise dosage form. This is essential in that it insures that the quantum of composition ingested by the animal is within the efficacious range. Moreover, the form in which the composition is administered eliminates many of the disadvantages generally encountered for the administration of ingestible flea repellent formulations. More specifically, by dissolving the garlic oil and Vitamin $B_1$ in a vegetable oil carrier and its subsequent placement in a soft gelatin capsule, the active components of composition are isolated, to a degree, and thus making them more palatable to the animal. This is in sharp contrast to the so called garlic tablets which must in fact be at least partially deodorized in order to make them acceptable for ingestion. In a soft gelatin capsule, garlic oil may be presented in its most aromatic (and thus, most effective) form, maintaining the offensive odor within the capsule until it dissolves in animals digestive tract. The capsule approach also insures freshness of the composition and provides a deterrent against tampering. In addition, since the generally offensive garlic component is encapsulated when ingested, the animal does not suffer from the associated bad breath which usually accompanies consumption of garlic. The dosage form of the composition is also water soluble, thus, insuring its more rapid and more complete absorption by the digestive system. This maybe particularly desirable in elderly or infirmed animals whose digestive abilities may be impaired. This is in sharp contrast to the garlic powders and tablets and brewer's yeast powders and tablets which are not readily water soluble, thereby reducing the bioavailability of the garlic and essential B vitamins in the digestive tract. This composition also has other unique advantages when compared to Brewer's yeast and other so called B complex type preparations. As is well known, the various B vitamins compete with one another in the digestive system for absorption and thus Vitamin $B_1$. Where it is present in such a mixture, is not as readily absorbed in thus "complex" environment as it would be where administered by itself or in combination with the garlic oil.

Upon absorption of the composition of this invention by the digestive system, its individual components are carried by the blood vessels throughout the body. It is known or suspected that Vitamin $B_1$ and garlic (and/or their respective metabolites) give off an insect repellent odor which is localized at the surface of the skin. Each of these components has been thought, by itself, to provide a degree of insect repellency, however, the extent to which they provide such protection has not been generally regarded to be sufficient to either prevent infestation by blood feeding pests or to rid the animal of such pests once infested.

As noted above, the compositions of this invention contain essentially two (2) ingredients which, in combination with one another, provide the ability to effectively prevent infestation of an animal with fleas and ticks and, if the animal is infested prior to the administration of this composition, to rid the animal of infestation of fleas and ticks. Because the composition is water soluble, the benefits incident to its ingestion are realized relatively quickly (generally within three (3) to six (6) hours after initial ingestion) resulting in control of the infestation within a day or two after the onset of treatment and the total elimination of such pest generally within four (4) to six (6) days after the onset of treatment. The maintenance of an essentially constant blood level of these ingredients, and/or the respective metabolites, provides continuous systemic protection of the animal from reinfestation without the attendant side effects of other systemic and topical preparations. In addition, because the compositions is ingested by the animal and consists essentially of natural ingredients, the animal's tolerance of composition is excellent, and no adverse side effects have been observed. Moreover, the benefits attendant with such method of administration also insure that the human contact with the animal does not evoke any adverse reaction incidental to such treatment. This is an extremely important advantage where the animal is a pet, and small children are in the household.

In order to more fully illustrate the advantages of this invention, the following Examples have been provided. Parts and percentages appearing in such Examples are by weight unless otherwise indicated. Apparatus (if any) and techniques used in the preparation of the composition and its evaluation are standard or as hereinbefore described.

EXAMPLE I

This study utilized 10 dogs each weighing 25-30 pounds. Each dog entered the study with moderate flea infestation (each was visually inspected and found to be infested with at least 8 fleas daily). During the study, no other flea therapy was used aside from those reported in the following data. The study lasted 12 weeks.

| PRIOR TO TESTING | | | | | | | |
|---|---|---|---|---|---|---|---|
| Week 1 | | | | | | | |
| Days | 1 | 2 | 3 | 4 | 5 | 6 | 7 |
| Average # of Fleas on Dog | 8 | 9 | 10 | 8 | 11 | 10 | 9 |
| DOGS GIVEN 10 mg. THIAMINE TWICE DAILY | | | | | | | |
| WEEK 2 | | | | | | | |
| Days | 1 | 2 | 3 | 4 | 5 | 6 | 7 |
| Average # of Fleas on Dog | 8 | 7 | 7 | 6 | 5 | 5 | 5 |
| DOGS GIVEN 15 mg. THIAMINE TWICE DAILY | | | | | | | |
| Week 3 | | | | | | | |
| Days | 1 | 2 | 3 | 4 | 5 | 6 | 7 |
| Average # of Fleas on Dog | 5 | 4 | 3 | 3 | 2 | 3 | 3 |
| DOGS GIVEN 20 mg THIAMINE TWICE DAILY | | | | | | | |
| Week 4 | | | | | | | |
| Days | 1 | 2 | 3 | 4 | 5 | 6 | 7 |
| Fleas on Dogs | 3 | 3 | 4 | 3 | 2 | 3 | 3 |
| 325 mg. GARLIC TABLETS TWICE DAILY | | | | | | | |
| Week 5 | | | | | | | |
| Days | 1 | 2 | 3 | 4 | 5 | 6 | 7 |
| Average # of Fleas on Dog | 4 | 5 | 5 | 4 | 5 | 4 | 5 |
| 325 mg. GARLIC OIL TWICE DAILY | | | | | | | |
| Week 6 | | | | | | | |
| Days | 1 | 2 | 3 | 4 | 5 | 6 | 7 |
| Average # of Fleas on Dog | 5 | 4 | 3 | 2 | 3 | 3 | 2 |
| 500 mg. GARLIC OIL TWICE DAILY | | | | | | | |
| Week 7 | | | | | | | |
| Days | 1 | 2 | 3 | 4 | 5 | 6 | 7 |
| Average # of Fleas on Dog | 2 | 2 | 2 | 3 | 2 | 3 | 2 |
| 325 mg. GARLIC OIL TWICE DAILY AND 15 mg. THIAMINE TWICE DAILY | | | | | | | |
| Week 8 | | | | | | | |
| Days | 1 | 2 | 3 | 4 | 5 | 6 | 7 |
| Average # of Fleas on Dog | 2 | 1 | 0 | 0 | 0 | 0 | 0 |
| 325 mg. GARLIC TABLETS TWICE DAILY AND 15 MG. THIAMINE TWICE DAILY | | | | | | | |
| Week 9 | | | | | | | |
| Days | 1 | 2 | 3 | 4 | 5 | 6 | 7 |
| Average # of Fleas on Dog | 0 | 1 | 2 | 2 | 2 | 1 | 2 |
| BREWERS YEAST AND GARLIC TABLETS "PET GUARD" | | | | | | | |
| Week 10 | | | | | | | |
| Days | 1 | 2 | 3 | 4 | 5 | 6 | 7 |
| Average # of Fleas on Dog | 3 | 4 | 6 | 6 | 7 | 6 | 8 |
| 325 mg. GARLIC OIL AND 15 MG. | | | | | | | |
| -continued | | | | | | | |
| THIAMINE TWICE DAILY | | | | | | | |
| Week 11 & 12 | | | | | | | |
| Days | 1 | 2 | 3 | 4 | 5 | 6 | 7 |
| Average # of Fleas on Dog | 5 | 4 | 2 | 2 | 1 | 1 | 0 |
| Days | 8 | 9 | 10 | 11 | 12 | 13 | 14 |
| Average # of Fleas on Dog | 0 | 0 | 0 | 0 | 0 | 0 | 0 |

What is claimed is:

1. A nutritional dietary supplement which, when ingested at regular intervals of about every 12 hours, affords essentially continuous protection of mammals from infestation by fleas and ticks, said supplement consisting essentially of an insect repellant effective amount of a mixture of aneurine and allium sativum, the relative proportion of aneurine to allium sativum in such mixture being at least about 1:20.

2. The dietary supplement of claim 1, wherein the aneurine and allium sativum are dissolved in a soybean oil carrier.

3. The dietary supplement of claim 1, wherein the aneurine and allium sativum are dissolved in a soybean oil carrier and and said effective amount of the resultant solution is contained within a water soluble capsule of a predetermined volume, thus providing a precise dosage form of the composition.

4. The dietary supplement of claim 3, wherein said insect repellant effective amount is at least about 1 milligram of aneurine and at least about 20 milligrams of allium sativum per pound of body weight of said mammal, administered on a daily basis, and about half the daily dose thereof is ingested by said mammal about every 12 hour.

5. A method for treatment of a mammal infested with ticks and fleas comprising:
(a) providing a mixture of aneurine and allium sativum, the relative weight ratio of aneurine to allium sativum in such mixture being at least 1:20; and
(b) orally administering about every twelve (12) hours, an effective dosage of the synergistic mixture to the mammal in a capsule form which provides a systemic level of each of said components of said mixture which is effective to repel said ticks and fleas.

6. The method of claim 5, wherein the orally-administered effective daily dosage is at least about one (1) milligram of aneurine per pound of mammal body weight and at least about 21 milligrams of allium sativum per pound of mammal body weight.

7. A nutritional dietary supplement which, when ingested by a mammal at regular intervals of about every 12 hours, affords continuous protection of said mammal from infestation by fleas and ticks, said supplement consisting essentially of an insect repellant effective amount of a mixture having two principal components, a first component comprising aneurine and a second component comprising allyl sulfide, the relative proportions of said components being at least 1:20 and each of said components being effective to enhance the insect repellant properties of the other so that the combined effect of the mixtures is greater than the insect repellant effect of each at the same or comparable concentrations, with the proviso that the concentration of aneurine in said mixture, based upon daily consumption of said supplement, is at least about one (1) milligram of aneurine per pound of body weight.

8. The dietary supplement of claim 7, wherein the aneurine and allyl sulfide are dissolved in a soybean oil carrier.

9. The dietary supplement of claim 7, wherein the aneurine and allyl sulfide are dissolved in a soybean oil carrier and the resultant solution contained within a water solution capsule of a predetermined volume, thus providing a precise dosage form of the composition.

10. A method of treatment of a mammal infested with ticks and fleas comprising:
   (a) providing a dietary supplement which includes a mixture of aneurine and allium sativum dissolved in a soybean oil base, said mixture consisting essentially of an insect repellant effectious amount of a synergistic mixture having two (2) principal components, a first component comprising aneurine and a second component comprising allyl sulfide, the relative proportions of said components in said mixture being at least 1:20 and each component being effective to enhance the insect repellent properties of the other so that the combined effect of the mixture is greater than the insect repellent effect of each component individually at the same or comparable concentrations, with the proviso that the concentration of aneurine in said mixture, based upon daily consumption of said supplement, is at least about one (1) milligram of aneurine per pound of body weight, and
   (b) orally administering about every twelve (12) hours, and effective dosage of the mixture to the mammal in a capsule form which provides a systemic level of each of said components of said mixture which is effective repel said ticks and fleas.

11. The method of claim 10, wherein said mixture is contained in a soft gelatin capsule.

* * * * *